US012515006B2

(12) United States Patent
McAuley et al.

(10) Patent No.: US 12,515,006 B2
(45) Date of Patent: Jan. 6, 2026

(54) HUMIDIFICATION BREATHING APPARATUS CONTROL

(71) Applicant: Fisher & Paykel Healthcare Limited, Auckland (NZ)

(72) Inventors: Alastair Edwin McAuley, Auckland (NZ); Igor Olegovich Yatsevich, Auckland (NZ); Nimansha Budhiraja, Auckland (NZ); Dongxue You, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 955 days.

(21) Appl. No.: 16/560,247

(22) Filed: Sep. 4, 2019

(65) Prior Publication Data

US 2020/0009347 A1 Jan. 9, 2020

Related U.S. Application Data

(63) Continuation of application No. 14/432,159, filed as application No. PCT/US2013/062762 on Sep. 30, 2013, now Pat. No. 10,441,740.

(Continued)

(51) Int. Cl.
*A61M 16/10* (2006.01)
*A61M 16/00* (2006.01)
(Continued)

(52) U.S. Cl.
CPC ...... *A61M 16/109* (2014.02); *A61M 16/0003* (2014.02); *A61M 16/06* (2013.01);
(Continued)

(58) Field of Classification Search
CPC ............ A61M 16/0003; A61M 16/109; A61M 16/06; A61M 16/16–168;
(Continued)

(56) References Cited

U.S. PATENT DOCUMENTS 3,326,214 A * 6/1967 Mccoy .............. A61M 16/1045 165/4
5,692,497 A * 12/1997 Schnitzer ............ A61M 16/024 128/207.14
(Continued)

FOREIGN PATENT DOCUMENTS

AU 2013323113 5/2018
EP 1005878 6/2000
(Continued)

OTHER PUBLICATIONS

DeWalle, David R.; Heisler, Gordon M. 1980. Water vapor mass balance method for determining air infiltration rates in houses. Research Note NE-301. Broomall, PA: U.S. Department of Agriculture, Forest Service, Northeastern Forest Experiment Station. 7 p. (Year: 1980).*
(Continued)

*Primary Examiner* — Paige Kathleen Bugg
(74) *Attorney, Agent, or Firm* — Knobbe Martens Olson & Bear LLP

(57) ABSTRACT

A humidification breathing apparatus for generating and delivering humidified air to a patient at a desired humidity proximate the patient, the apparatus comprising an air flow path and a controller for controlling operation of the humidification breathing apparatus, wherein the controller is configured to operate the humidification breathing apparatus to control humidity at a point in the flow path to achieve the desired delivered humidity proximate the patient based on the patient exhaled humidity and flow.

17 Claims, 9 Drawing Sheets

Related U.S. Application Data

(60) Provisional application No. 61/707,629, filed on Sep. 28, 2012.

(51) Int. Cl.
*A61M 16/06* (2006.01)
*A61M 16/16* (2006.01)

(52) U.S. Cl.
CPC ....... *A61M 16/16* (2013.01); *A61M 2016/003* (2013.01); *A61M 2016/0039* (2013.01); *A61M 2016/0042* (2013.01); *A61M 16/0051* (2013.01); *A61M 16/0069* (2014.02); *A61M 16/026* (2017.08); *A61M 16/1095* (2014.02); *A61M 16/161* (2014.02); *A61M 2205/3334* (2013.01); *A61M 2205/3368* (2013.01); *A61M 2205/502* (2013.01); *A61M 2230/50* (2013.01)

(58) Field of Classification Search
CPC ........ A61M 16/1095; A61M 2016/003; A61M 2205/3334; A61M 2205/3368; A61M 16/0051; A61M 16/026; A61M 2016/0039; A61M 2016/0042; A61M 2230/50
USPC ...................................... 128/203, 14, 203.14
See application file for complete search history.

(56) References Cited

U.S. PATENT DOCUMENTS

| | | | | |
|---|---|---|---|---|
| 7,051,733 | B2 * | 5/2006 | Gradon | A61M 16/161 128/203.17 |
| 9,186,477 | B2 * | 11/2015 | Hunt | A61M 16/0875 |
| 10,130,787 | B2 * | 11/2018 | Hunt | A61M 16/1085 |
| 2008/0078388 | A1 | 4/2008 | Vandine | |
| 2008/0190426 | A1 | 8/2008 | Koch | |
| 2009/0107496 | A1 | 4/2009 | McGhin et al. | |
| 2009/0223514 | A1 * | 9/2009 | Smith | A61M 16/026 128/203.14 |
| 2010/0275919 | A1 * | 11/2010 | Sung | A61M 16/161 128/204.22 |
| 2010/0294279 | A1 * | 11/2010 | Ionascu | A61N 5/10 128/203.26 |
| 2011/0120462 | A1 * | 5/2011 | Tatkov | A61M 16/161 128/203.14 |
| 2011/0220105 | A1 | 9/2011 | Meier | |
| 2012/0017904 | A1 * | 1/2012 | Ratto | A61M 16/024 128/207.18 |
| 2012/0174922 | A1 * | 7/2012 | Virr | A61M 16/106 128/206.28 |
| 2014/0166006 | A1 * | 6/2014 | Meier | A61M 16/16 128/203.14 |
| 2015/0217079 | A1 | 8/2015 | Mcauley et al. | |
| 2015/0238716 | A1 * | 8/2015 | Budhiraja | A61M 16/0633 128/203.14 |
| 2016/0015927 | A1 * | 1/2016 | Winski | A61M 16/109 128/203.14 |
| 2025/0152901 | A1 | 5/2025 | Mcauley et al. | |

FOREIGN PATENT DOCUMENTS

| | | | |
|---|---|---|---|
| EP | 2897677 | 11/2020 | |
| JP | 2011/125618 | 6/2011 | |
| WO | WO 2001/091841 | 12/2001 | |
| WO | WO-2007101298 A1 * | 9/2007 | A61M 16/00 |
| WO | WO 2013/124803 | 8/2013 | |
| WO | WO 2014/052983 | 4/2014 | |

OTHER PUBLICATIONS

Examination Report for AU Application No. 2020202230, dated Feb. 26, 2021; 4 pages.
Examination Report for CA Application No. 2,886,596, dated Mar. 11, 2021; 4 pages.
Extended European Search Report for Application No. 20185023.7 dated Jan. 21, 2021; 7 pages.
Examination Report for Application No. AU 2020202230 dated Aug. 28, 2020; 5 pages.
Office Action for Japanese No. 2019-110781; 4 pages.
International Search Report; PCT/US2013/062762; dated Jan. 7, 2014; 3 pages.
Written Opinion; PCT/US2013/026762; dated Jan. 7, 2014; 4 pages.
Australian Examination Report; dated May 1, 2017, 4 pages.
Translation of Examination Report for Japanese Application No. 2015-534807 dated Jul. 26, 2017 (4 pages).
Examination Report for Australian Patent Application No. 2018202966 dated Jan. 23, 2019 in 4 pages.
European Examination Report; dated Apr. 15, 2019, 5 pages.
Control Theory, Wikipedia (Year: 2018).
Canadian Examination Report; dated Jul. 16, 2019, 5 pages.

* cited by examiner

HUMIDIFICATION BREATHING APPARATUS CONTROL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF INVENTION

The present invention relates to humidification breathing apparatus and their control to provide humidified air to a patient at a desired humidity and temperature.

BACKGROUND OF INVENTION

In breathing apparatus that provide humidification, the intention is to provide humidified air to the patient at a desired humidity and/or temperature to achieve the desired patient comfort and/or therapy. Providing the desired humidity and/or temperature requires achieving and maintaining the humidity and/or temperature of humidified air at the patient (that is, in the vicinity of the patient's mouth and/or nose) as this is the humidity and temperature of air that is ultimately passed to the patient. (NB: "in the vicinity" can also be termed "at or near" or "proximate".) In theory, this involves heating and/or humidifying air that passes through the flow path of the breathing apparatus from the flow generator to the patient (via e.g. the conduit and patient interface) until the desired humidity and/or temperature proximate the patient is achieved and maintained.

However, while controlling the humidity and/or temperature proximate the patient is possible, it is technically and economically difficult. For example, using sensors to detect the humidity and/or temperature of humidified air proximate the patient is expensive and has technical and health difficulties. Therefore, traditionally it is not the humidity and/or temperature of the humidified air proximate the patient that is controlled, but rather the humidity and/or temperature of humidified air at some other point in the flow path, being a point that is easier to monitor. A target temperature and/or humidity is determined for a particular point (such as the humidifier outlet or the end of the conduit/hose), and it is that temperature and/or humidity that is controlled. The difficulty with this approach is that achieving and maintaining the target temperature and/or humidity at the point in the flow path does not guarantee that the desired humidity and/or temperature are achieved proximate to the patient and delivered to them. The humidity and/or temperature of humidified air can change by the time it reaches the patient. For example, if the temperature and/or humidity of air at the end of the conduit is kept at a target, the humidity and temperature fluctuations provided in the patient interface mean that the actual temperature and/or humidity delivered to the patient via the patient interface varies in a unknown manner from that at the end of the hose. This makes it difficult to know the actual temperature/humidity of air at the patient and makes it difficult to deliver the desired temperature and/or humidity of humidified air to the patient.

SUMMARY OF INVENTION

It is an object of the invention to provide a humidification breathing apparatus and/or method of operation that controls humidity and/or temperature of humidified air in a flow path in a manner that improves the ability to deliver humidified air to the patient at the desired humidity and/or temperature.

In one aspect the present invention may be said to consist in a humidification breathing apparatus for generating and delivering humidified air to a patient at a desired humidity proximate the patient, the apparatus comprising: an air flow path, and a controller for controlling operation of the humidification breathing apparatus, wherein the controller is configured to operate the humidification breathing apparatus to control humidity at a point in the flow path to achieve the desired delivered humidity proximate the patient based on the patient exhaled humidity and flow.

Preferably the apparatus further comprises a conduit coupled to a patient interface that form part of the flow path.

Preferably the point in the flow path where the controller is configured to control humidity is at or near the patient interface end of the conduit.

Preferably the patient interface is a mask and the controller controls the humidity at the point in the flow path to achieve a target humidity calculated from patient exhaled humidity and flow, the relationship between target humidity, patient exhaled humidity and flow being based on the balance of water vapour mass flow into and out of the mask.

Preferably the water vapour mass flow is:

$$\underbrace{\left(\dot{m}_M^{H_2O}\right)}_{flow\ out} = \underbrace{\left(\dot{m}_P^{H_2O}\right) + \left(\dot{m}_C^{H_2O}\right)}_{flow\ in},\ [\text{mg } H_2O \text{ sec}^{-1}] \quad (14)$$

Where:

The water vapour mass flow out averaged over 1 breathing cycle $$\left(\dot{m}_M^{H_2O}\right)$$

equals the amount of water vapour present in air mixed in the mask and goes out through the exhaust/bias holes.

The water vapour mass flow from patient averaged over 1 breathing cycle $$\left(\dot{m}_P^{H_2O}\right)$$

is a function of CPAP delivered humidity, patient exhaled humidity and patient peak flow.

The water vapour mass flow from the CPAP apparatus averaged over 1 breathing cycle $$\left(\dot{m}_C^{H_2O}\right)$$

is a function of CPAP delivered humidity and average/bias flow and peak flow.

Preferably the relationship is defined by:

$$EOH\_AH=f(A,J_B,M_h,h_P) \quad (5)$$

Where $h_P$ is the humidity provided by the patient (exhalation) into the mask

A is the peak flow of the patient $J_B$ is the average flow (bias plus leak flow)

$M_h$ is the mask humidity

EOH_AH is the end of hose (absolute) humidity

Preferably the relationship is defined by:

$$EOH\_AH=(Mask\_AH-(A/(J_B*pi))*Patient\_AH)/(1-A/(J_B*pi)) \quad (6)$$

where

A is the patient peak flow j is the average flow

Patient_T and Patient_AH are the temperature and humidity of the air exhaled by the patient.

Preferably the point in the flow path where the controller is configured to control humidity is at or near the humidifier outlet.

Preferably the apparatus comprises a flow sensor to sense the flow.

Preferably the flow comprises one or more characteristics of flow, being one or more of:

average flow rate, peak flow rate, tidal volume.

Preferably patient exhaled humidity is one or more of:

a predetermined value, a sensed value using a sensor, a calculated value from one or more of: BMI, height, weight, body volume or any other suitable physiological patient characteristic.

Preferably the controller is configured to operate the humidifier to control humidity by controlling a heater plate temperature, for example by controlling the duty cycle of the power supplied to the heater plate.

Preferably the controller is further configured to operate the humidification breathing apparatus to control humidity based on mask information, for example, mask internal volume.

In another aspect the present invention may be said to consist in a method of generating and delivering humidified air to a patient at a desired humidity proximate the patient comprising operating a humidification breathing apparatus to control humidity at a point in a flow path to achieve the desired delivered humidity proximate the patient based on the patient exhaled humidity and flow.

Preferably controlling humidity at the point in the flow path is to achieve a target humidity calculated from patient exhaled humidity and flow, the relationship between target humidity, patient exhaled humidity and flow being based on the balance of water vapour mass flow into and out of the mask.

In another aspect the present invention may be said to consist in a humidification breathing apparatus for generating and delivering humidified air to a patient at a desired humidity proximate the patient, the apparatus comprising: an air flow path, and a controller for controlling operation of the humidification breathing apparatus, wherein the controller is configured to operate the humidification breathing apparatus to control humidity at a point in the flow path to achieve the desired delivered humidity proximate the patient based on the patient exhaled humidity and flow, and wherein the controller is configured to operate the humidification breathing apparatus to control temperature at a point in the flow path to achieve the desired delivered temperature proximate the patient based on the patient exhaled temperature and flow.

In another aspect the present invention may be said to consist in a method of generating and delivering humidified air to a patient at a desired humidity proximate the patient comprising: operating a humidification breathing apparatus to control humidity at a point in a flow path to achieve the desired delivered humidity proximate the patient based on the patient exhaled humidity and flow, and operating a humidification breathing apparatus to control temperature at a point in the flow path to achieve the desired delivered temperature proximate the patient based on the patient exhaled temperature and flow.

In another aspect the present invention may be said to consist in a humidification breathing apparatus for generating and delivering humidified air to a patient at a desired temperature proximate the patient comprising: an air flow path, and a controller for controlling operation of the humidification breathing apparatus, wherein the controller is configured to operate the humidification breathing apparatus to control temperature at a point in the flow path to achieve the desired delivered temperature proximate the patient based on the patient exhaled temperature and flow.

Preferably the apparatus further comprises a conduit coupled to a patient interface that form part of the flow path.

Preferably the point in the flow path where the controller is configured to control temperature is at or near the patient interface end of the conduit.

Preferably the patient interface is a mask and the humidifier controls the temperature at the point in the flow path to achieve a target temperature calculated from patient exhaled temperature and flow, the relationship between target temperature, patient exhaled temperature and flow being based on the balance of heat flow into and out of the mask.

Preferably the heat flow is:

$$\underbrace{\langle \dot{q}_M \rangle + \langle \dot{q}_{loss} \rangle}_{\text{average ``heat'' out}} = \underbrace{\langle \dot{q}_P \rangle + \langle \dot{q}_C \rangle}_{\text{``heat'' in}}, \; [J \ \sec^{-1}] \quad (15)$$

Where

The heat out comprises the heat energy carried by the air flow out through the bias holes $J_B$ (function of mask temperature and average flow) and also the heat lost to the ambient through the mask surface (function of mask temperature, ambient temperature and the heat loss coefficient through the mask).

The heat in comprises the heat energy carried by CPAP flow (function of average flow, peak flow and CPAP delivered temperature) and the heat energy carried by patient flow into the mask (function of patient exhaled temperature, CPAP delivered temperature and patient peak flow).

Preferably the relationship is defined by:

$$EOH\_T=f(A,J_B,M_t,T_P,T_A) \quad (11)$$

Where $T_P$ is the temperature provided by the patient (exhalation) into the mask A is the peak flow of the patient $J_B$ is the average flow (bias plus leak flow)

$T_A$ is ambient temperature as measured by e.g. a sensor $M_t$ is the mask temperature EOH_T is the end of hose temperature Preferably the relationship is defined by $$EOH\_T=(Mask\_T*(1+\theta)-(A/(J_B*pi))*Patient\_T-*Amb\_T)i(1-A/(J_B*pi) \quad (12)$$

Where—

$$\theta \equiv \frac{k_{eff}\, S}{\rho_M C_P^M} J_B^{-1}$$

$k_{eff}$ is the effective heat conduction coefficient through the mask,

S is the surface area of the mask

Cp and ρ refer to the air specific heat and (average) density at constant (average) process pressure A is the patient peak flow J is the average flow Patient_T and Patient_AH are the temperature and humidity of the air exhaled by the patient.

Preferably the point in the flow path where the controller is configured to control temperature is at or near the humidifier outlet.

Preferably the apparatus further comprises a flow sensor to sense the flow.

Preferably the flow comprises one or more characteristics of flow, being one or more of:

average flow rate, peak flow rate, tidal volume.

Preferably patient exhaled temperature is one or more of:

a predetermined value, a sensed value using a sensor, a calculated value from one or more of: BMI, height, weight, body volume or any other suitable physiological patient characteristic.

Preferably the controller is configured to operate the humidifier to control temperature by controlling energising a heater in the conduit or alternatively by energising a heater plate apparatus, to heat the delivered humidified air.

Preferably the controller is further configured to operate the humidifier to control temperature based input air temperature, and optionally wherein the input air temperature is ambient air temperature or a predetermined value.

Preferably the controller is further configured to operate the humidification breathing apparatus to control humidity based on mask information, optionally wherein the mask information is one or more of:

mask internal volume, mask surface area, mask material.

In another aspect the present invention may be said to consist in a method of generating and delivering humidified air to a patient at a desired temperature proximate the patient comprising operating a humidification breathing apparatus to control temperature at a point in the flow path to achieve the desired delivered temperature proximate the patient based on the patient exhaled temperature and flow.

Preferably the temperature at the point in the flow path is to achieve a target temperature calculated from patient exhaled temperature and flow, the relationship between target temperature, patient exhaled temperature and flow being based on the balance of heat flow into and out of the mask.

In another aspect the present invention may be said to consist in a humidification breathing apparatus with a flow path for delivering humidified air to a patient at a desired humidity proximate the patient, wherein the humidifier comprises a controller configured to control humidity at a point in the flow path to achieve the desired delivered humidity proximate the patient based on the contribution a patient makes to humidity.

In another aspect the present invention may be said to consist in a method of controlling a humidification breathing apparatus to deliver a desired humidity to a patient comprising receiving input on patient exhaled humidity and flow and operating the humidification breathing apparatus to provide an output humidity based on the patient exhaled humidity and flow.

In another aspect the present invention may be said to consist in a humidification breathing apparatus with a flow path for delivering humidified air to a patient at a desired temperature proximate the patient, wherein the humidifier comprises a controller configured to control temperature at a point in the flow path to achieve the desired delivered temperature proximate the patient based on the contribution a patient makes to temperature.

In another aspect the present invention may be said to consist in a method of controlling a humidification breathing apparatus to deliver a desired temperature to a patient comprising receiving input on patient exhaled temperature and flow and operating the humidification breathing apparatus to provide an output temperature based on the patient exhaled temperature and flow.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Where specific integers are mentioned herein which have known equivalents in the art to which this invention relates, such known equivalents are deemed to be incorporated herein as if individually set forth.

BRIEF DESCRIPTION OF THE DRAWINGS

Embodiments of the invention will now be described with reference to the following drawings, of which.

DETAILED DESCRIPTION OF PREFERRED EMBODIMENTS

Overview of Invention

The present invention relates to a humidification breathing apparatus and method of its operation for supplying humidified air to a patient. The specification of the priority application U.S. 61/707,629 is incorporated herein by reference into this specification in its entirety. The humidification breathing apparatus could be a humidifier on its own, or a humidifier combined with other hardware to provide additional breathing assistance, such as a CPAP (continuous positive airway pressure) apparatus, Auto titration apparatus, bi-level apparatus or other PAP apparatus operating at e.g. 3 to 20 cm $H_2O$ or similar or high flow breathing apparatus with a humidifier. The humidification breathing apparatus and its method of operation generates and delivers humidified air to a patient at (also deemed to mean "or close to") a desired humidity and/or temperature. The humidification breathing apparatus and its method of operation aim to achieve a desired humidity and/or temperature of the humidified air is that actually delivered to the patient. That is, the humidification breathing apparatus and method of operation control the humidity and/or temperature of humidified air in the air flow path such that the humidified air proximate/proximal (that is at or near) the patient is at the desired humidity and/or temperature.

Figure 1A:
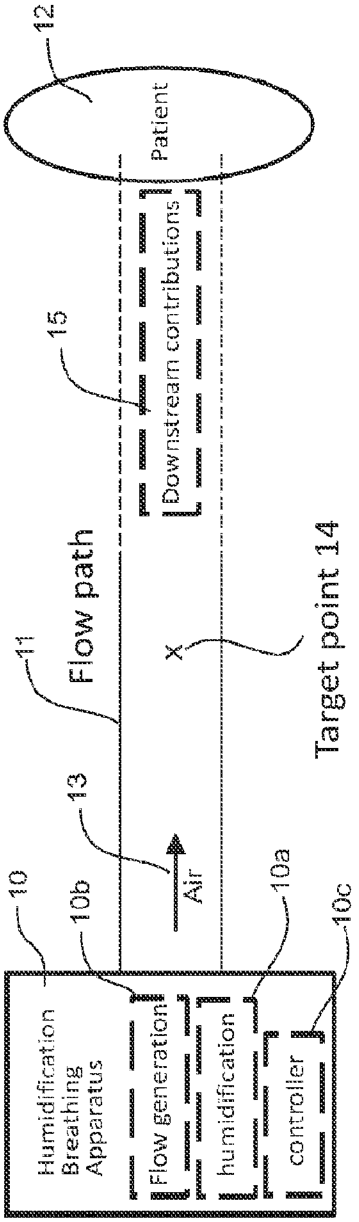
FIG. 1A is a schematic diagram of a humidification breathing apparatus that provides humidified air to a patient along a flow path that has downstream contributions that alter humidity and/or temperature of humidified air.

Referring to FIG. 1A, the humidification breathing apparatus has air humidification capabilities (box 10), comprising a humidifier for humidification 10*a*, flow generator 10*b* and controller 10*c*, along with hardware for other capabilities such as CPAP or the like. A flow path 11 delivers humidified air 13 to the patient 12. The flow path is shown separate to the breathing apparatus box 10, but it can be considered part of the breathing apparatus, and the flow path can include parts of the hardware itself, such as internal ducting and air paths within the humidifier. The patient interface can also be considered part of the flow path and humidification breathing apparatus in general. In general terms, the temperature and/or humidity of humidified air 13 is controlled at some point (target point) 14 in the humidification breathing apparatus flow path. Models of the downstream contributions 15 to humidity and/or temperature provided by components and inputs (e.g. patient inputs) further down the remaining parts of the flow path (ending at the patient) are determined and target temperature/humidity models are devised and implemented in the controller 10*c*.

A target temperature and/or humidity at the target point is determined from the models. This target temperature and/or humidity is determined using the models such that if the target temperature and/or humidity is reached, the remaining contributions 15 to humidity and temperature from downstream influences bring the actual temperature and/or humidity proximate the patient to (or close to) the desired values. The humidification breathing apparatus and/or any peripheral components (such as fans, heated tubes, masks and the like) are operated to control the humidity and/or temperature of humidified air passing through the humidification breathing apparatus flow path so that the target temperature and/or humidity at the target point are achieved and maintained.

The target temperature and/or humidity of the air in the flow path can be achieved using any of the usual control methods for a humidification breathing apparatus, such as using closed loop feedback (using sensors or the like) or using models or other predictive mechanisms.

Figure 1B:
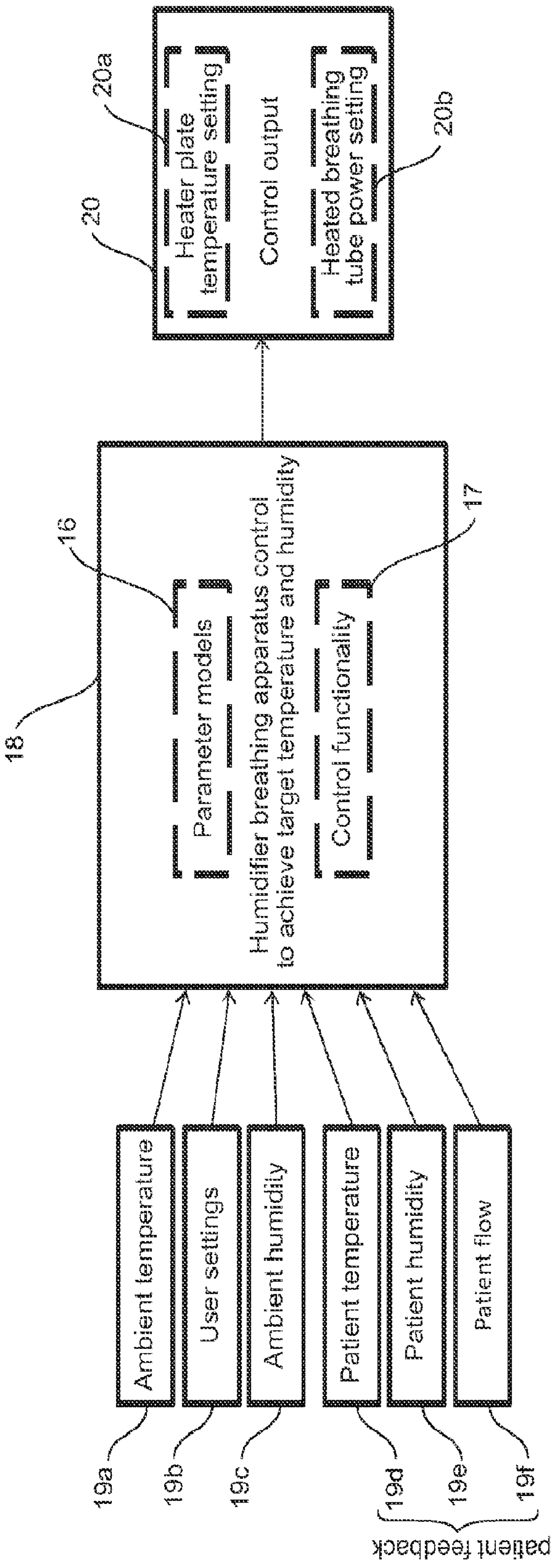
FIG. 1B is a schematic diagram showing general humidification breathing apparatus control.

Referring to FIG. 1B, humidification breathing apparatus control 18 is provided to achieve the required desired temperature and humidity at the patient. The control comprises (parameter) models 16 for determining relevant values of parameters that must be achieved to deliver the desired temperature and humidity at the patient, and control functionality (e.g. in the form of models/equations) 17 to operate the humidification apparatus to achieve those parameter values. The models comprise patient contribution/target parameter models 16, and humidification breathing apparatus control models for e.g. controlling the apparatus heater plate temperature and breathing tube heater power. The humidification breathing apparatus control 18 among other things uses ambient temperature 19*a*, user settings 19*b*, ambient humidity 19*c*, and patient feedback comprising patient flow 19*f*, patient temperature 19*d*, patient humidity 19*e*. Control output parameters 20, signals or other control mechanisms are output 20, such as heater plate temperature 20*a* and heated breathing tube power 20*b*, which are used to control the humidification breathing apparatus operation to achieve the desired temperature and humidity at the patient.

In calculating the target temperature/humidity the relevant model(s) in effect takes into account the contribution of the patient to the humidity and temperature of the humidified air. The contribution may be due, for example, to the temperature and/or humidity of the patient breath and also breath flow characteristics (also termed "flow" or "patient flow" or "flow characteristics"). Other parameters can optionally be used also, including those relating to the mask type itself. For example, a parameter(s) could comprise mask internal volume, mask surface area, and/or mask material. Using the patient contribution, the controller 109 (see FIG. 3) can calculate the required target temperature and/or humidity of the air at some other point in the air flow path which if achieved will achieve the desired parameters of humidified air at/delivered to the patient.

1 First Embodiment of Invention

1.1 Overview

Figure 3:
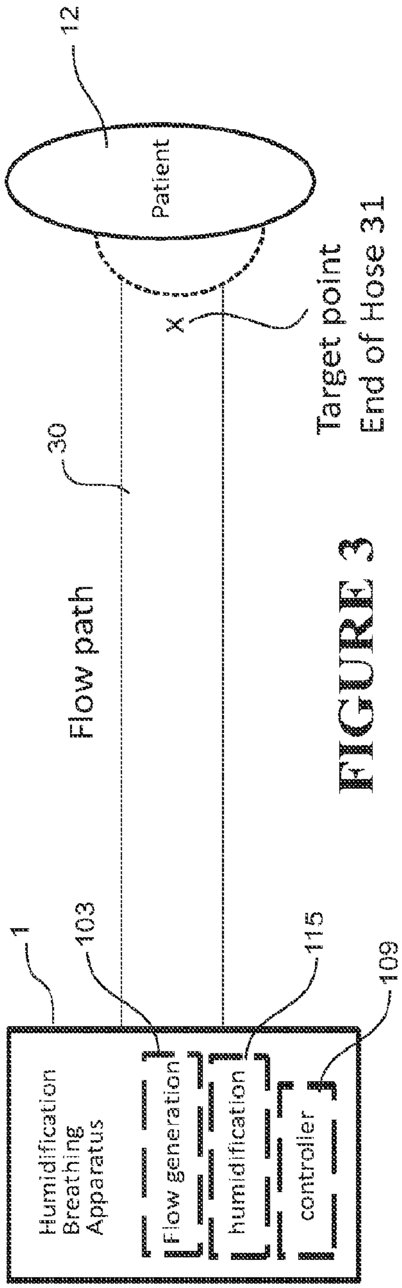
FIG. 3 is a high level schematic generalisation of a humidification breathing apparatus such as that shown in FIG. 2 that provides humidified air to a patient according to one embodiment.
Figure 2:
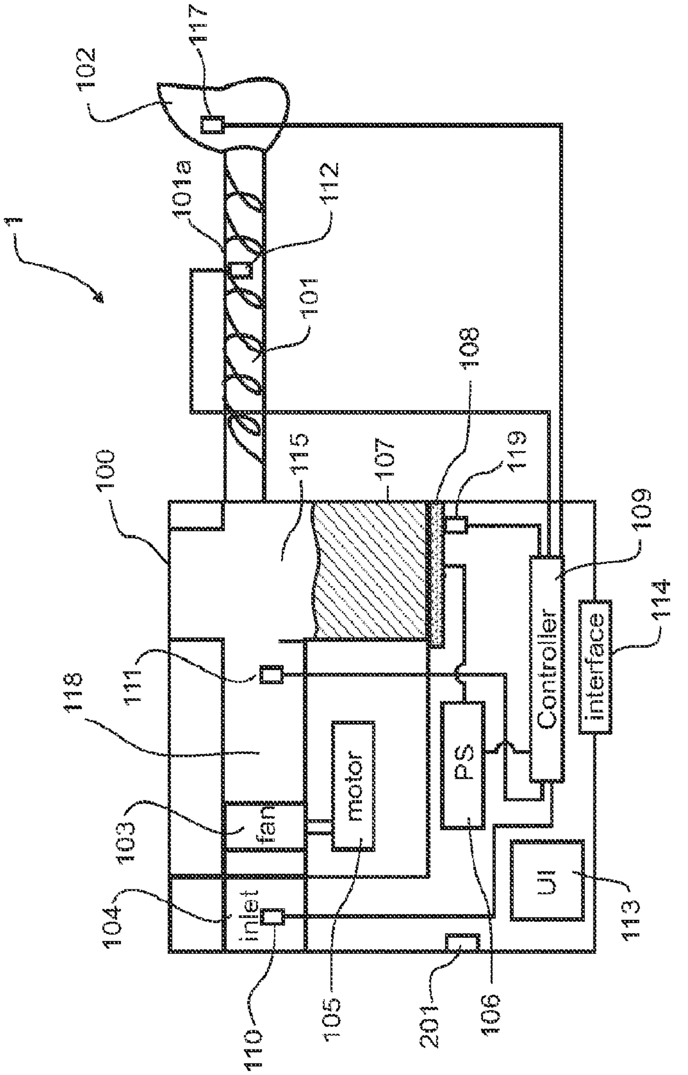
FIG. 2 is a detailed schematic diagram of a CPAP apparatus with a humidifier that provides pressurised humidified air to a patient.
Figure 4:
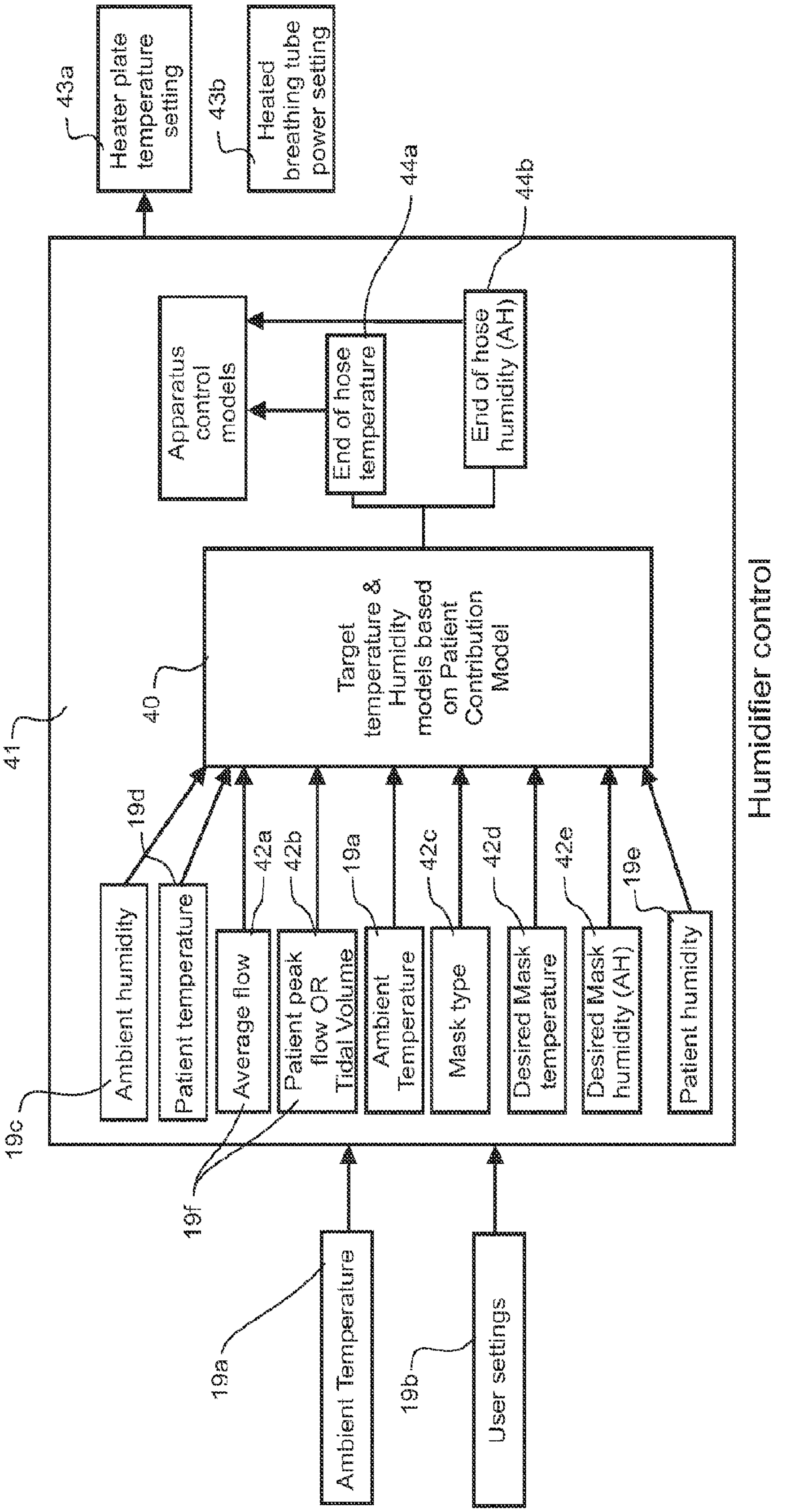
FIG. 4 is a schematic diagram of humidification breathing apparatus control.

A possible non-limiting embodiment of a humidification breathing apparatus is shown in overview in FIGS. 2 to 4. In this case, it is a CPAP apparatus 1 with integrated humidifier as shown in FIG. 2. It will be appreciated that any sort of breathing apparatus that provides humidification could be used, including a flow therapy apparatus with humidification or even a humidifier alone.

FIG. 2 shows a block diagram illustrating one embodiment of a humidification breathing apparatus 1, comprising a PAP apparatus 100 for delivering a supply of breathing gases, a breathing conduit 101, which comprises a heater, and a patient interface 102.

The breathing conduit 101 (also called a "hose" or "tube") extends from an outlet in the PAP apparatus 100 and to the patient interface 102. The patient interface may be any suitable sealing patient interface such as a full face mask, nasal mask, direct nasal mask, oral mask or the like, with bias flow holes for a bias flow rate that is kept constant during both the inhalation and exhalation phases by maintaining constant pressure at the mask.

The PAP apparatus comprises a blower 103. The blower preferably comprises a fan driven by an electric motor. Air is drawn into the PAP apparatus through the inlet 104 by the fan. Pressurised air leaves the fan for supply to the patient. Alternatively, controllable flow generators may draw on a source of high pressure gas, and regulate a flow of gas from the high pressure source.

The PAP apparatus comprises a humidifier 115. In alternative embodiments, the humidifier 115 may be separate from the PAP apparatus and part of the PAP apparatus. The humidifier 115 as shown is a pass over type humidifier where air passing through the humidifier picks up a quantity of water vapour from a reservoir of water 107. The water reservoir is heated by a heater 108. The humidifier is preferably integrated into the housing of the PAP apparatus. Alternatively the humidifier may be a separate component within the housing of the PAP apparatus or separate from the PAP apparatus with a conduit connecting between the PAP apparatus and the humidifier. Other types of humidifiers, other than a pass over type may be used. In some forms multiple humidifiers may used. The humidified air leaves the end of heated breathing tube 101 (later referred as end of hose, EOH), it is mixed with the patients' exhaled breathe and then flows out of the bias hole on a nasal, full face or oral mask 102. In some embodiments a non heated breathing tube could be used instead.

The PAP apparatus comprises a controller 109. The controller 109 is used to control the humidification breathing apparatus, including the PAP apparatus, tube heater 101*a*, and other peripherals. It also operates the model(s) of the present invention. The controller receives inputs from a user interface (UI) 113 and sensors. The user interface could be in the form of any suitable user interface such as a knob, a plurality of buttons, a screen or any combination thereof.

The user interface allows the PAP apparatus to display information to the user and also allows a user to input information to the PAP apparatus, more particularly to the controller. The controller may also be provided with an interface 114 for connecting to an external data source.

The controller comprises inputs for receiving inputs from one or more sensors (such as 112, 110, 201, 111, 117, 119 as shown), which can comprise temperature, flow, humidity and/or pressure sensors upstream or downstream to the fan or outside the apparatus. As shown a flow sensor determines the flow characteristics (such as volume, velocity or phase) of gases supplied to the patient or user. The flow sensor may be positioned upstream 110 or downstream 111, 112 to the fan. Ambient temperature and humidity sensors 201, 110 can also be used—which can be at the blower inlet, humidifier inlet or any other suitable location. Optionally end of hose 112 and/or mask 117 temperature and/or humidity sensors can be used as required. Optionally a heater plate temperature sensor 119 is used. The sensors shown are one configuration of sensors that can be used. Any other configuration of sensors and any other types of sensors may be used.

There may be fewer or more sensors than those shown. Sensors can be provided in any suitable location to sense any of flow, humidity, temperature and/or pressure or the like of the patient (e.g. patient exhaled flow measured in the mask or at any other suitable point), humidified or unhumidified flow at any point in the flow path, ambient surroundings or at any other point in the apparatus or peripheral components. The apparatus is powered by a power supply.

The humidification breathing apparatus comprises an air flow path 30, which can comprise any part in which air 13 flow travels. That can comprise the blower inlet, the blower 103, ducting to the humidifier 118, flow path through the water chamber 115, outlet ducts from the water chamber, the conduit 101 and the patient interface 102. In this embodiment, the desired temperature and humidity is that in the mask near the patient's nose/mouth—this is the temperature and humidity that will be delivered to the patient. The target point is a suitable point in that air flow path, which in this embodiment is the end of the conduit (termed "end of hose" 31 see FIG. 3), as this is a point in the flow path in which humidity and/or temperature can be controlled to a target value. The patient interface is a full face, nasal or oral mask. The mask 102 itself and the patient provide contributions such that the humidity and/or temperature at the end of the conduit differ from those proximate the patient (that is, in the mask and near the mouth/nose). Due to e.g. the heat loss from the end of hose to the mask and also due to the addition of humidity and heat from patient's exhalation into the mask space, the relative humidity of the air in the mask can be much higher than the end of the hose. This can cause condensation in the mask if the relative humidity exceeds 100%.

Referring to FIG. 3, the humidification apparatus of FIG. 2 is modelled as an apparatus with an air flow path 30 and downstream patient/mask contributions that effect humidity and temperature of air flow. The patient contributions (and/or optionally mask contributions) are used to derive models that determine the target temperature and/or humidity at the end of the conduit (based on inputs) that will result in the desired mask temperature and humidity. Referring to FIG. 4, which is an embodiment of the general case shown in FIG. 1B, the controller implements (among other functionality) the models 40 as part of an overall humidifier control program 41 to determine target temperature and/or humidity at the target point 31 (that will achieve the desired temperature and humidity in the mask) and to control the heater plate 108 and breathing tube power 101*a* to achieve/maintain the target temperature and/or humidity at the target point 31. The desired temperature and humidity (that is mask humidity and temperature) are taken as inputs into the model 42*d*, 42*e* (desired mask temperature and humidity). Also taken as inputs can be one or more of ambient temperature 19*a*, ambient humidity 19*c*, average flow 42*a*, patient peak flow or tidal volume 42*b*, and optionally mask type 42c, patient temperature 19*d*, patient humidity 19*e* and the like.

In this embodiment, the controller is configured to determine both a target temperature and humidity and is configured to achieve/maintain these both at the target point. However, in alternative embodiments, the controller might be programmed to only determine and achieve a target temperature, or to determine and achieve a target humidity, instead of both. Where both target temperature and humidity are required, the controller could be configured with a single model to determine and control both, or separate models to determine and control each separately (as is the case with the present embodiment). Where only one of target temperature or humidity are required, a separate model is used.

1.2 Detailed Description of First Embodiment

The embodiment will now be described in more detail with reference to FIGS. 5 to 10.

1.2.1 General Description of Target Temperature and Humidity Model

Figure 5:
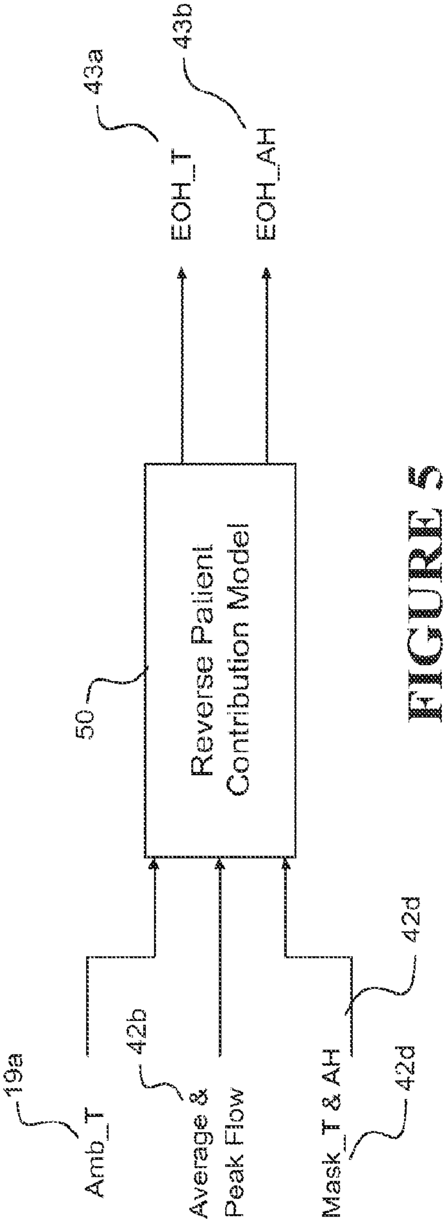
FIG. 5 is a schematic diagram of a target temperature and humidity model used in the control shown in FIG. 4.

The present embodiment uses separate models to determine the target temperature and humidity, so that these parameters can be determined and controlled in separate implementations. However, first a brief description of a combined target temperature and humidity model will be described with reference to FIGS. 5 and 6A, 6B for overview purposes and also to support the discussion on how the models are derived. (FIG. 5 is a simplified version of the model shown in FIG. 4 as part of the overall control.) Following that, a detailed description of the separate models is provided for determining target temperature and humidity. But this is only provided for illustrative purposes and should not be considered limiting.

As noted previously, in this embodiment, the desired temperature is the temperature in the mask, and is termed "mask temperature ($M_t$) or (Mask_T)". The desired humidity is the humidity in the mask and is termed "mask (absolute) humidity ($M_h$) or (mask_AH)". These are specified by patient/physician settings or determined using measured parameters or determined using a combination of both. Determination of these parameters is described later. Referring to FIG. 5, once determined, $M_h$, $M_t$ become known parameters that are inputs 42*d*, 42*e* into a target humidity and temperature model 50 that is based on (a "reverse") of the patient contribution model for humidity and temperature, along with other inputs to produce the end of conduit (hose) (target) humidity (EOH_AH) 44*b* and temperature (EOH_T) 44*a*. The inputs to the model 50 also optionally include patient_temperature 19*d* and patient_absolute humidity (AH) 19*e*-being the temperature and humidity of the air exhaled by the patient. Rather than direct inputs these can be included intrinsically in the model (as is the case in FIG. 5), but can still be considered model inputs. As an example, average values obtained from literature (e.g. 34° C., 85%, 32 mg/L) could be used. Also, mask type or mask parameters can be an input to the model, where the mask type is detected by CPAP or entered by user. But, in an alternative implementation, an average mask type is used to simplify the model. Alternatively, the values can be calculated using physiological patient characteristics/parameters such as height, weight, age, BMI, inhaled temperature or humidity, tidal volume, nose or mouth breathing, lung disease (e.g. COPD), rhinitis/cold, bronchial blood flow, hydration level.

Figure 6A:
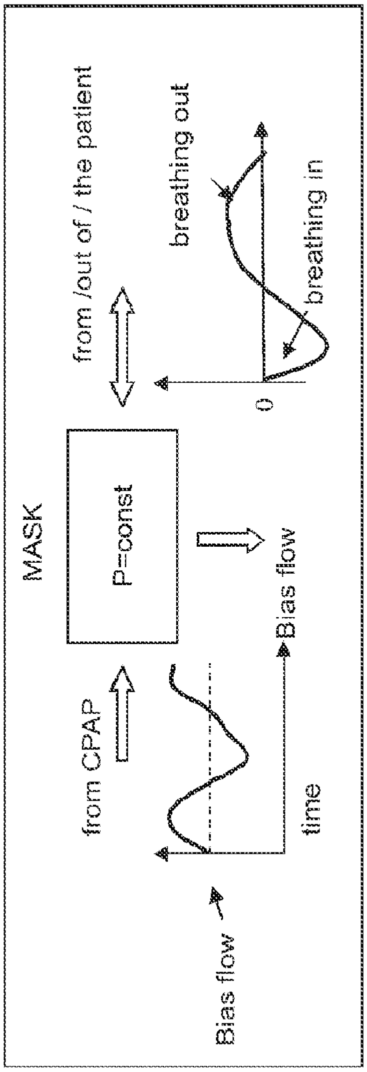
FIGS. 6A, 6B are schematic diagrams showing the flow balance in the mask of a humidification breathing apparatus.
Figure 6B:
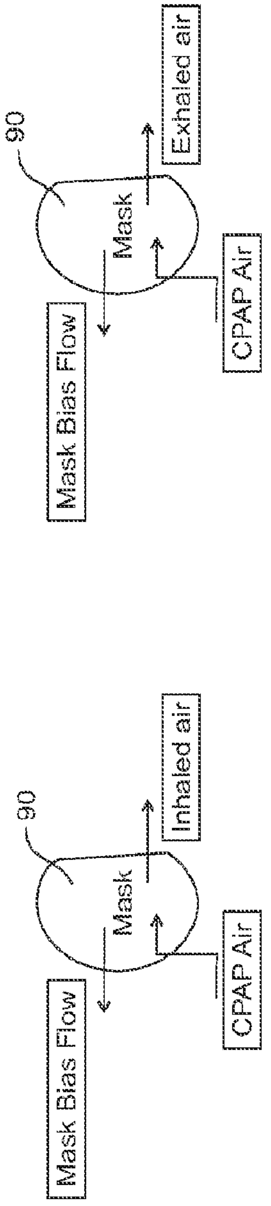

The model 50 is based on the following. For a balanced system, the flow provided by the CPAP breathing apparatus will equal the negative sum of patient flow and average/bias flow. This is shown in FIGS. 6A, 6B. There is an incoming CPAP flow into the mask and an outgoing flow out of the bias hole at the constant rate. FIGS. 6A, 6B illustrates the air flow in an inhalation and exhalation process where the mask is considered as a control volume.

Figure 7:
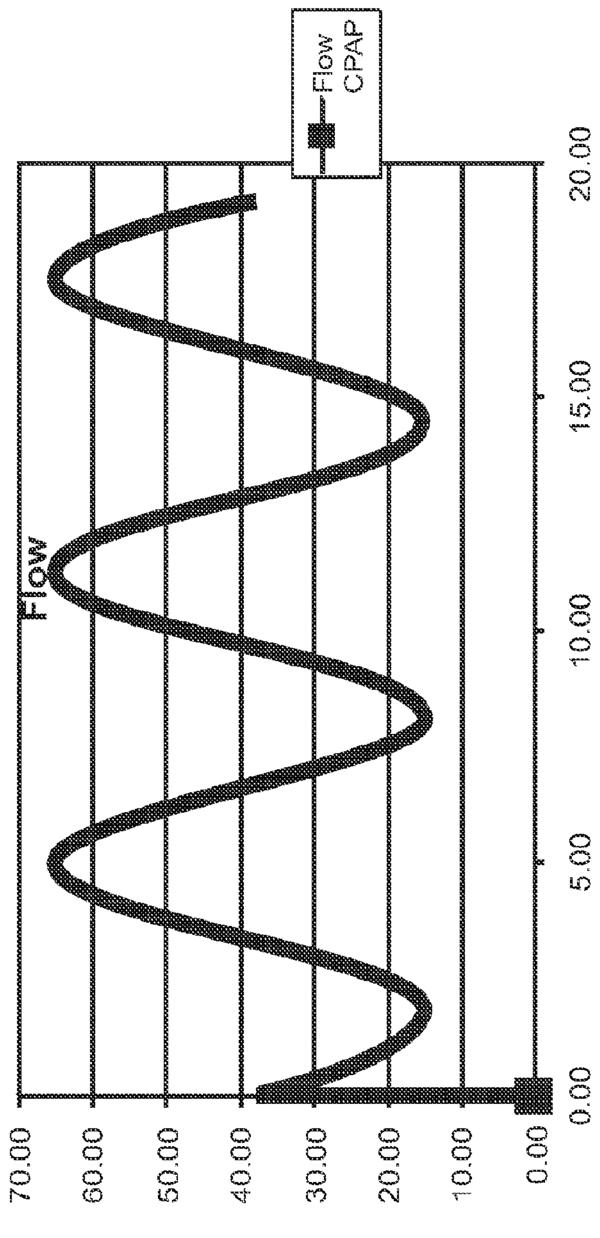
FIG. 7 shows a sine wave approximation of breath flow.

The patient flow can be approximated by a sine curve for the purposes of the model. The CPAP flow waveform is shown in FIG. 7. The average flow can be assumed to be constant.

According to conservation of mass, assuming density remains the same, the volume flow in the system can be represented by the following equation:

$$V_{CPAP}+V_{patient}+V_{bias}=0 \tag{16}$$

This is equivalent to equation 13 below.

CPAP flow mostly has a positive sign representing flow into the system whereas the bias flow should always have a negative sign representing flow out of the system. The patient's flow has a positive sign during exhalation and a negative sign during inhalation. However, with a particularly large volume exhalation, the CPAP flow can reverse its direction and flows back into the apparatus, resulting in a negative flow.

EOH air temperature and humidity level can be considered as a known input parameter in this particular analysis. Also the sensor measurements of real time CPAP flow and bias flow rate that are available from the controller can be taken as input parameter (flow characteristics). Another input factor is the ambient room condition which would be assumed to be constant for the analysis. The exhaled air composition for an average patient is largely dependent on the patient of interest and varies considerably from individual to individual. Most studies done to date suggest that a temperature of 34-35 degree Celsius and a humidity level of 75-95% in exhaled air are universally acceptable values. Rather than assuming an average breathing pattern for patients, we will calculate the average flow, and amplitude (or peak flow) based on the detected CPAP and bias flow rates and model the breath pattern using a suitable function like sine/cosine. Some of the model inputs can be determined from using the CPAP flow waveform. For example, the average flow can be obtained by calculating a moving average of the dynamic flow over 749 samples or more (15 sec with 10 ms sensor sampling). The peak flow for each breath can be obtained by calculating the difference between maximum flow and average flow for each breath. To get an average peak flow, a moving average of this peak flow can be calculated over 15 breaths or over a set time period. Peak flow could also be calculated from physiological parameters, such as those mentioned earlier.

The above combined target temperature and humidity model was provided by way of overview. The models of this embodiment will now be described in detail as separate models below.

1.2.2 Target Humidity Model

Figure 8:
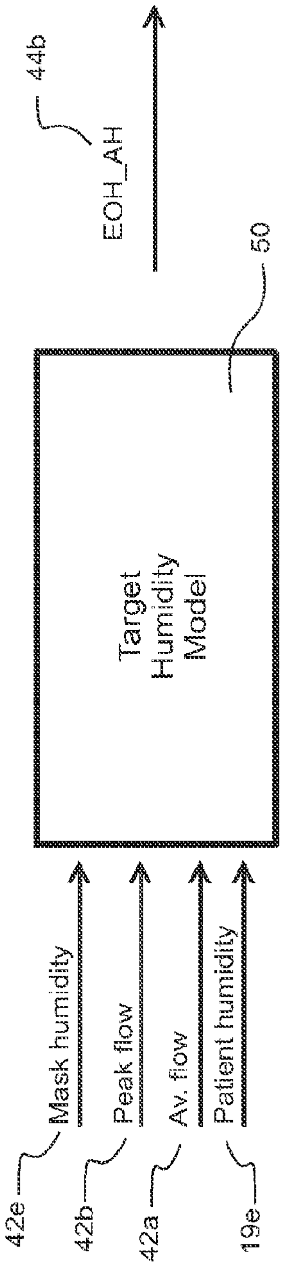
FIG. 8 is a schematic diagram of a target humidity model, which may form part of the model in FIG. 5.

Referring to FIG. 8, once determined, $M_h$ becomes a known parameter that is an input to a target humidity model that is based on (a "reverse") of the patient contribution model for humidity, along with other inputs to produce the end of conduit (hose) (target) humidity (EOH_AH) 44*b*.

The patient contribution model for humidity can be generally defined as the following function:

$$M_h=f(\text{flow characteristic},h_C,h_P) \tag{1}$$

Where:

$h_C$ is the humidity provided by the CPAP apparatus to the mask—in this case the humidity at the end of the hose (also EOH_AH).

$h_P$ is the humidity provided by the patient (exhalation) into the mask flow characteristic represents any one or more breath flow characteristics of the patient The patient contribution model is rearranged to the following function that defines the target humidity model 50:

$$\text{EOH\_AH}=f(\text{flow characteristic},M_h,h_P) \tag{2}$$

In one embodiment, a functional definition of a patient contribution model that specifies the actual flow characteristics is as follows:

$$M_h=f(A,J_B,h_C,h_P) \quad (3)$$

Where

A is the peak flow of the patient $J_B$ is the average flow (bias plus leak flow)

Mask type can also additionally be used as an input, but this is not essential and an average for a mask can be used instead and included intrinsically in the function.

One example of this function is, as based on water vapour mass balance is:

$$AH_{mask}V_{mask}+AH_{CPAP}V_{CPAP}+AH_{patient}V_{patient}=AH_{mixture}V_{total} \quad (4a)$$

Since the volume of the mask is constantly flushed with the incoming air, the residual term ($AH_{mask}V_{mask}$)=0. Therefore, the equation will be as follows:

$$AH_{CPAP}V_{CPAP}+AH_{patient}V_{patient}=AH_{mixture}V_{total} \quad (4b)$$

Solving for end of hose (absolute) humidity, the functional definition of the patient contribution model (3) that specifies the actual flow characteristics can be rearranged to (as shown in FIG. 8):

$$EOH\_AH=f(A,J_B,M_h,h_P) \quad (5)$$

A particular instance of the function in equation (5) can be implemented by the following equation:

$$EOH\_AH=(Mask\_AH-(A/(J_B*pi))*Patient\_AH)/(1-A/(J_B/*pi)) \quad (6)$$

Where—

A is the patient peak flow $J_B$ is the average flow

Patient_T and Patient_AH are the temperature and humidity of the air exhaled by the patient.

Therefore, equation (6) is one implementation of a target humidity model to determine the target humidity at the end of hose target point.

1.2.3 TARGET Temperature Model

Figure 9:
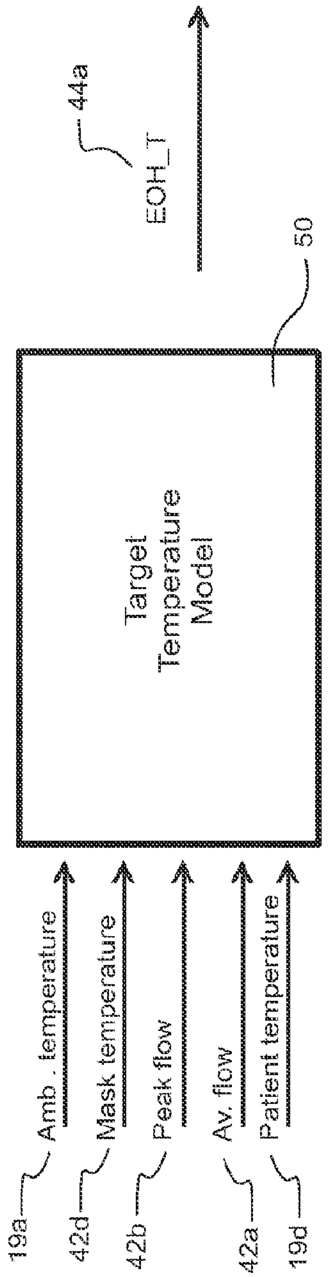
FIG. 9 is a schematic diagram of a target temperature model, which may form part of the model in FIG. 5.

Referring to FIG. 9, once determined, $M_t$ becomes a known parameter that is an input to a target temperature model that is based on (a "reverse") of the patient contribution model for temperature, along with other inputs to produce the end of conduit (hose) (target) temperature (EOH_T) 44*a*.

The patient contribution model for temperature can be generally defined as follow:

$$M_t=f(\text{flow characteristic},T_C,T_P) \quad (7)$$

Where:

$T_C$ is the temperature provided by the CPAP apparatus to the mask—in this case the temperature at the end of the hose (EOH_T) 44*a*.

$T_P$ is the temperature provided by the patient (exhalation) into the mask

Flow characteristic represents any one or more breath flow characteristics of the patient The patient contribution model is rearranged to the following function that defines the target temperature model 50:

$$EOH\_T=f(\text{flow characteristic},M_t,T_P) \quad (8)$$

In one embodiment, a functional definition of a patient contribution model that specifies the actual flow characteristics is as follows:

$$M_t=f(A,J_B,T_C,T_P,T_A) \quad (9)$$

Where

A is the peak flow of the patient $J_B$ is the average flow (bias plus leak flow)

$T_A$ is ambient temperature as measured by e.g. a sensor

Mask type can also additionally be used as an input, but this is not essential and an average for a mask can be used instead and included intrinsically in the function.

One example of this function based on energy balance equation is:

$$\Delta(m_{mask}C_pT_{mask})=\dot{m}_{CPAP}C_pT_{CPAP}+\dot{m}_{Patient}C_pT_{Patient}-\dot{m}_{bias}C_pT_{mask}-\dot{Q}_{Lost} \quad (10a)$$

(Change in the energy of air in the mask=Energy of air coming in from CPAP+Energy of air coming in from patient−Energy of air going out through the bias holes−Heat lost to ambient)

In steady state, the change in the energy of air in the mask $\Delta(m_{mask}C_pT_{mask})$ will be 0. So the equation will be as follows:

$$\dot{m}_{bias}C_pT_{mask}+\dot{Q}_{lost}=\dot{m}_{CPAP}C_pT_{CPAP}+\dot{m}_{patient}C_pT_{Patient} \quad (10b)$$

Solving for end of hose temperature, the functional definition of the patient contribution model (9) that specifies the actual flow characteristics can be rearranged to:

$$EOH\_T=f(A,J_B,M_t,T_P,T_A) \quad (11)$$

A particular instance of this function can be implemented by the following equation:

$$EOH\_T=(Mask\_T*(1+\theta)-(A/(J_B*pi))*Patient\_T-\theta*Amb\_T)/(1-A/(J_B*pi)) \quad (12)$$

Where—

$$\theta \equiv \frac{k_{eff}\,S}{\rho_M C_P^M} J_B^{-1}$$

$k_{eff}$ is the effective heat conduction coefficient through the mask,

S is the surface area of the mask

Cp and ρ refer to the air specific heat and (average) density at constant (average) process pressure A is the patient peak flow $J_B$ is the average flow Patient_T and Patient_AH are the temperature and humidity of the air exhaled by the patient.

Therefore, equation (12) is one implementation of a target temperature model to determine the target humidity at the end of hose target point.

Therefore, equations (6), (12) can be used to determine target humidity and temperature respectively, which can then be achieved using control methods programmed in to the controller. Alternatively, a neural network can also be used to determine target humidity and temperature with the inputs described above.

1.2.4 Derivation of Target Humidity and Temperature Models

The derivation of the patient contribution, target temperature and target humidity models will now be described.

1.2.4.1 Background Definitions

The following abbreviations are used:

Indices: "C"—"CPAP", "P"—"Patient", "B"—"bias (flow)", "M"—what is there in the mask (mixed), "A"—"Ambient", Jx, x=C, P, B—volumetric flow, hx, x=C, P, M—absolute humidity, mg $H_2O$ $L^{-1}$ air, Tx, x=C, P, M—temperature, ° C.

$V_{LUNG}$ is the tidal volume per breath and br_period is the time period of the breath, RF is the respiration frequency.

Referring to FIGS. 6A, 6B, according to law of conservation of mass, the system shown can be written as follows, assuming air densities remain the same.

$$J_C(t)+J_P(t)-J_B=0, \quad (13)$$

With the exhaust pressure being constant (atmospheric), the $J_B$ is now also constant. For the illustration purposes and simplicity, a sinusoidal time-dependence of the flow in/out of the lungs for patient flow $J_P=A\sin(\omega t)$ is assumed, where A is the amplitude or patient peak flow.

Figure 11A:
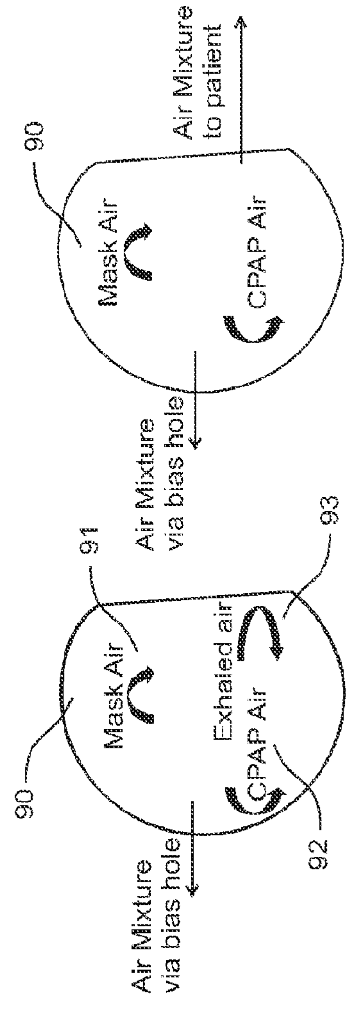
FIGS. 11A, 11B are schematic diagrams showing the flow balance in the mask of a humidification breathing apparatus.

Referring to FIG. 11*a*, considering the mask 90 as an open system or a control volume, the thermodynamic interactions that are involved are largely the mixing of different fluids. During the exhalation phase, the residual air inside the mask 91 (i.e. mixture resultant from last breathe cycle) is mixed with the incoming CPAP air 92 and patient exhaled air 93 whereas during the inhalation phase, the residual air inside the mask is mostly flushed out by the large volume of incoming CPAP air. This is a mass convection and diffusion process as shown in FIG. 11*a*.

Figure 11B:
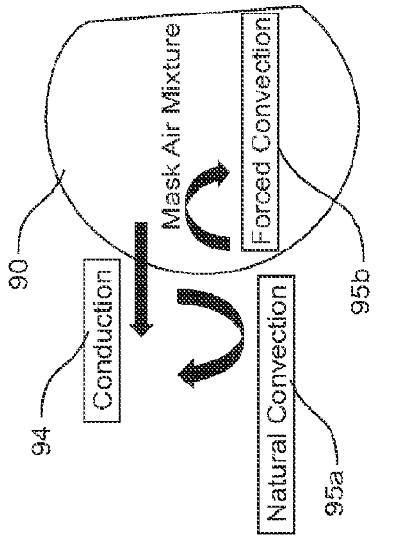

In most CPAP apparatus operating environments, the room would have a lower temperature than the air inside the mask, resulting in a heat exchange out of the system. The breath cycle can be considered as a thermodynamic cyclic process, assuming each exhalation is relatively similar and any mask residual air is flushed out by the incoming CPAP air during inhalation, bringing the mask condition back to an initial state. Thus, the average air temperature inside the mask averaged out for each cycle of inhalation and exhalation processes should maintain approximately constant. For this reason, a steady-state heat transfer process involving convection 95*a*, 95*b* and conduction 94 is considered as shown in FIG. 11*b*.

The above-mentioned thermodynamic process in the sealed mask is likely to be turbulent mixing due to the nature of rapid variation of velocity in the small space. Turbulence is an effective aid in the process of molecular mixing as the flow motion induces a large interfacial surface area promoting the diffusion process.

Turbulence mixing is normally categorised into three levels: (1) passive mixing such as mixing of match-density fluids, (2) mixing that is coupled to the dynamics such as Rayleigh-Taylor instability flows in the case of different-density fluids in an acceleration field, and (3) mixing that changes the fluid such as a pressure increase. Inside-mask air mixing falls in the first category as the fluids involved (i.e. air) are of similar density. For such mixing process, the analysis of the mixing is not required to describe the flow dynamics. Thus, we do not need to consider the change in flow pattern during each breath cycle due to the mixing process.

1.2.4.2 Derivation of Target Humidity Model

Water vapour mass (m) rate balance averaged over 1 breathing cycle then is:

$$\underbrace{\left\langle \dot{m}_M^{H_2O} \right\rangle}_{flow\ out} = \underbrace{\left\langle \dot{m}_P^{H_2O} \right\rangle + \left\langle \dot{m}_C^{H_2O} \right\rangle}_{flow\ in}, \ [\text{mg H}_2\text{O sec}^{-1}] \quad (14)$$

Where:

The Water vapour mass Flow out averaged over 1 breathing cycle $$\left\langle \dot{m}_M^{H_2O} \right\rangle$$

equals the amount of water vapour present in air mixed in the mask and goes out through the exhaust/bias holes.

The Water vapour mass Flow from patient averaged over 1 breathing cycle $$\left\langle \dot{m}_P^{H_2O} \right\rangle$$

is a function of CPAP delivered humidity, patient exhaled humidity and patient peak flow.

The water vapour mass flow from the CPAP apparatus averaged over 1 breathing cycle $$\left\langle \dot{m}_C^{H_2O} \right\rangle$$

is a function of CPAP delivered humidity and flow characteristics, such as average/bias flow and/or peak flow.

Due to the complexity of the geometry, a simplification can be made. The scalar conservation of mass of water vapour at some discrete points during the breathing cycle is applied. This assumes that the incoming CPAP air is mixed well with the exhaled air and the residual air inside the mask before leaving via the bias hole. The mathematical representation is as the following: (water vapour mass flow into the mask equals water vapour mass flow out)

$$AH_{mask}V_{mask}+AH_{CPAP}V_{CPAP}+AH_{patient}V_{patient}=AH_{mixture}V_{total} \quad (4a)$$

Since the volume of the mask is constantly flushed with the incoming air, the residual term $(AH_{mask}V_{mask})=0$. Therefore, the equation will be as follows:

$$AH_{CPAP}V_{CPAP}+AH_{patient}V_{patient}=AH_{mixture}V_{total} \quad (4b)$$

From the above equation, the average humidity of the air in the mask can be written as.

$$\text{Mask Humidity}=\text{function}(A,J_B,h_C,h_P) \quad (3)$$

Solving the above equation for target humidity, results in.

$$\text{EOH\_AH}=f(A,J_B,M_h,h_P) \quad (5)$$

and $$\text{EOH\_AH}=(\text{Mask\_AH}-(A/(J_B*pi))*\text{Patient\_AH})/(1-A/(J_B*pi)) \quad (6)$$

as previously stated.

1.2.4.3 Derivation of Target Temperature Model

Using the same approach for temperature, a heat energy balance equation for the mask system can be written as below:

$$\underbrace{\left\langle \dot{q}_M \right\rangle + \left\langle \dot{q}_{loss} \right\rangle}_{average\ \text{"heat" out}} = \underbrace{\left\langle \dot{q}_P \right\rangle + \left\langle \dot{q}_C \right\rangle}_{\text{"heat" in}}, \ [J\ \text{sec}^{-1}] \quad (15)$$

Where

The heat out comprises the heat energy carried by the air flow out through the bias holes $J_B$ (function of mask temperature and average flow) and also the heat lost to the ambient through the mask surface (function of mask temperature, ambient temperature and the heat loss coefficient through the mask).

The heat in comprises the heat energy carried by CPAP flow (function of average flow, peak flow and CPAP delivered temperature) and the heat energy carried by patient flow into the mask (function of patient exhaled temperature, CPAP delivered temperature and patient peak flow).

It will be assumed that the mixing air process is completed before the air leaves the system via the bias hole during both inhalation and exhalation. The exhalation phase is the process when the mixed air gains more heat and humidity.

1. The mask temperature obtained from the last time step would be used to calculate the mask temperature at the current time step, thus giving an iterative model represented by the following equation.

2. The model output gives the mask air temperature as a function of time during each breathe-cycle and the average value is calculated and compared with the experimental measurement. However, the results showed errors mostly in one-direction.

From the second law of thermodynamic, it is known that heat flows from higher-temperature object to lower-temperature object. For most of the CPAP operating environments, the air inside the mask is likely to have a higher temperature than the ambient room temperature, and there would be heat lost from inside of the mask to the ambient.

The energy balance equation including the heat loss is as follows:

$$\Delta(m_{mask}C_pT_{mask})=\dot{m}_{CPAP}C_pT_{CPAP}+\dot{m}_{Patient}C_pT_{Patient}-\dot{m}_{bias}C_pT_{mask}-\dot{Q}_{lost} \quad (10a)$$

(Change in the energy of air in the mask=Energy of air coming in from CPAP+Energy of air coming in from patient−Energy of air going out through the bias holes−Heat lost to ambient)

In steady state, the change in the energy of air in the mask $\Delta(m_{mask}C_pT_{mask})$ will be 0. So the equation will be as follows:

$$\dot{m}_{bias}C_pT_{mask}+\dot{Q}_{lost}=\dot{m}_{CPAP}C_pT_{CPAP}+\dot{m}_{patient}C_pT_{Patient}(10b)$$

Using the concept of thermal resistance:

$$R_{in}=\frac{Q_{lost}}{(T_{mask}-T_{inWall})}. \quad 1$$

$$R_{cond}=\frac{Q_{lost}}{(T_{inWall}-T_{outWall})}. \quad 2$$

$$R_{out}=\frac{Q_{lost}}{(T_{outWall}-T_{amb})}. \quad 3$$

Due to the complex geometry of the mask, it is very difficult to calculate these thermal resistances theoretically. Therefore, an empirical approach was taken to obtain a statistical relationship for the thermal resistance using experimental measurements.

Solving the above equation for mask temperature, the average temperature of the air in the mask can be written as:

$$\text{Mask Temperature}=\text{function}(A,J_B,T_C,T_P,T_A) \quad (9)$$

Solving the above equation for target temperature, results in $$\text{EOH\_}T=f(A,J_B,M_t,T_P,T_A) \quad (11)$$

and:

$$\text{EOH\_}T=(\text{Mask\_}T^*(1+\theta)-(A/(J_B{}^*pi)^*\text{Patient\_}T-\theta^*\text{Amb\_}T)(1-A/(J^*pi)) \quad (12)$$

as previously stated.

$k_{eff}$ and $S_{mask}$ were measured experimentally for a nominal mask type for this particular implementation. In alternative variations, mask type can be included as an input to the model, where the mask type is detected by CPAP or $T_p$ and $h_p$ are the temperature and absolute humidity of the air exhaled by the patient. For one implementation, average values obtained from literature (i.e. 34° C., 85%, 32 mg/L) can be used, for example.

1.2.5 Humidification Breathing Apparatus Control

Figure 10:
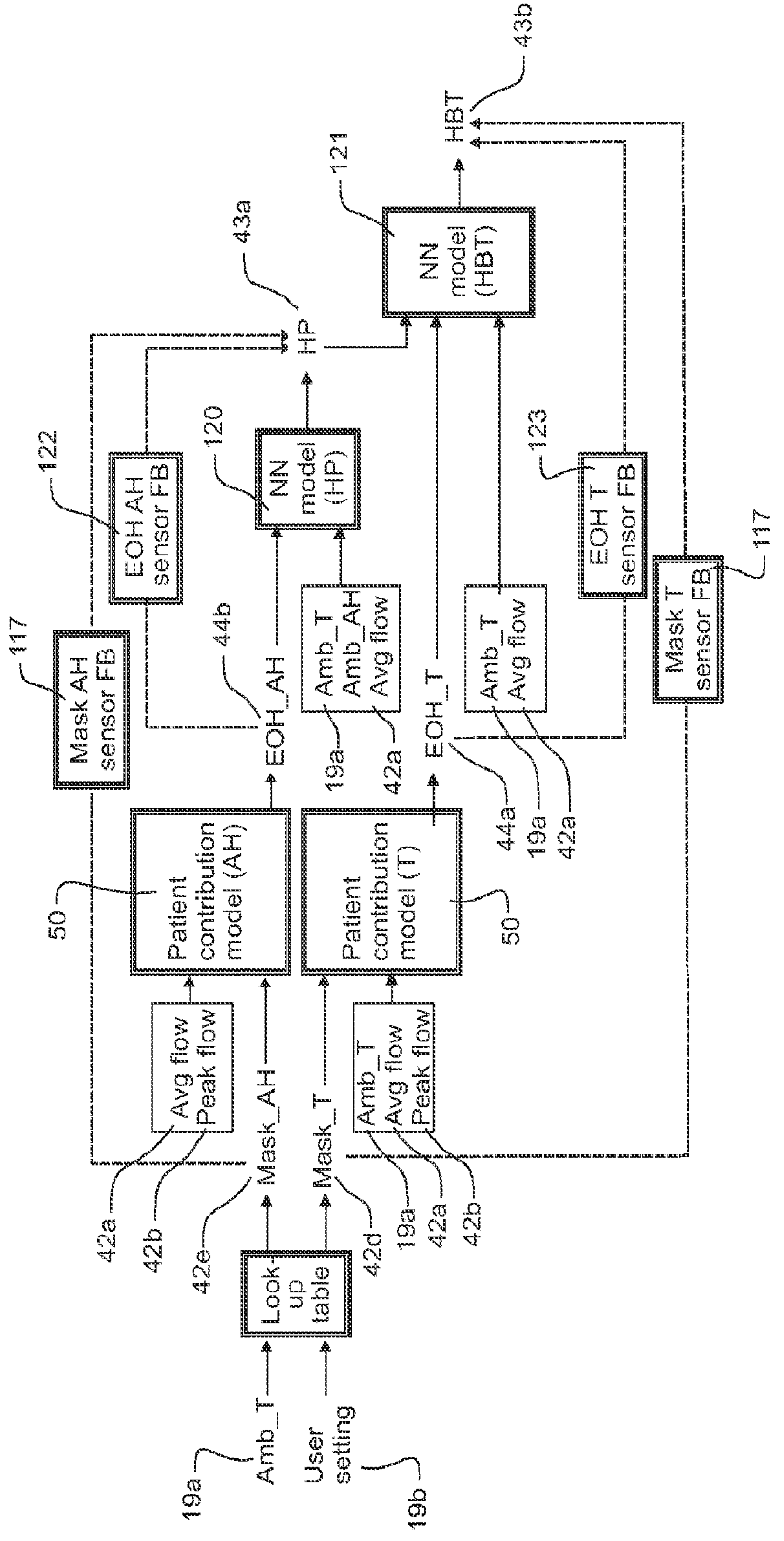
FIG. 10 is a schematic process flow diagram of the overall humidification breathing apparatus control.

The controller is configured to implement the models above using equations (6), (12) to determine the target temperature and humidity at the end of the hose. Once those targets have been determined, the controller is also configured to operate the humidification breathing apparatus to achieve those targets at the target point (end of hose). This was shown in overview in FIG. 4, and a detailed example of the overall apparatus control (implemented by the controller) for this embodiment is shown in FIG. 10.

Referring to those Figures, a user or physician inputs the preferred temperature and/or humidity settings into the humidification breathing apparatus via the user input control interface 114. Ambient temperature 19*a* is also received as an input into the controller, for example from a temperature sensor situated outside the breathing apparatus. The controller 109 contains a look up table or similar implementation that uses the ambient temperature 19*a* and user settings 19*b* to determine the desired mask humidity 42*e* and temperature 42*d*. For example, the mask relative humidity (Mask_RH) and also mask temperature (Mask_T) 42*d* and mask absolute humidity (Mask_AH) 42*e* are pre-determined for each comfort setting for ambient temperatures from 5° C. to 35° C. and these are programmed into the controller look-up table. These values are defined based on feedback from patient trials or other empirical methods. The desired Mask_T 42*d* and Mask_AH 42*e* can be determined using two look-up tables in the unit memory for each user setting and different ambient temperatures.

Next, the controller 109 uses the desired mask humidity 42*e* and temperature 42 *d* as inputs into the equations (6), (12) that implement the target temperature and humidity models 50. The controller 109 also uses average flow 42*a*, peak flow 42*b* and ambient temperature 19*a* as inputs into those equations as received from the appropriate sensors/inputs. The target temperature and target humidity models 50 then output the target end of hose humidity (EOH_AH) 44*b* and temperatures (EOH_T) 44*a* as described previously.

The controller 109 then operates the humidification breathing apparatus to achieve and maintain the target humidity and temperature. In this embodiment, the controller does this by controlling the heater plate (HP) 108 to control target humidity and the heater (HBT) 101*a* in the breathing tube to control target temperature. To control the heater plate 108 to achieve the target humidity, the controller 109 uses the target humidity (end of hose temperature 44*a*) along with ambient temperature 19*a*, ambient humidity 19*c* (measured by sensor or determined through a model) and average flow 42*a* as inputs into a neural network model or equations 120 that outputs the target heater plate temperature 43*a* that will achieve the target end of hose humidity 44*b*. The controller 109 also optionally uses an end of hose humidity sensor 122 reading as a feedback input into the model 120. Similarly, to control the heated breathing tube to achieve the target temperature (end of hose temperature

44*a*), the controller 109 uses the target temperature along with ambient temperature 19*a*, and average flow 42*a* and heater plate temperature 43*a* as inputs into a neural network model or equations 121 that outputs the target power 43*b* for the heated breathing tube 101 to achieve the target end of hose temperature 44*a*. It also optionally or as an alternative uses an end of hose temperature sensor 123 reading as a feedback input into the model 121. Based on the heater plate target temperature 43*a* and HBT target power 43*b*, the controller 109 generates and passes control voltages to the heater plate 108 and breathing tube heater 101*a* respectively to control them to attain and maintain the target heater plate temperature 43*a* and breathing tube power 43*b* to achieve the target temperature/humidity at the end of hose 44*a*, 44*b*.

The above embodiment could be run as an open loop system, where no sensors are present to measure the output humidity and temperature. However, optionally, there can be sensors present to measure humidity and/or temperature in the mask or end of hose. If they are present, the following occurs.

If a sensor 117 is implemented to measure temperature in the mask 102, the HBT power 43*b* will be adjusted according to the feedback control loop to maintain target mask temperature 42*d*. In this case, the target temperature model (1) 50 and neural network model (HBT) 121 would be bypassed. In this case, just the target humidity model 50 and neural network model 120 for the heater plate 108 would be used.

Similarly, if a sensor 117 is implemented to measure humidity (AH or RH) in the mask 102, the HP temperature/power 43*a* would be adjusted according to the feedback control loop to maintain target mask humidity 42*e*. In this case, the target humidity model (AH) 50 and neural network model (HP) 120 would be bypassed. In this case, just the target temperature model 50 and neural network model 121 for the breathing tube heater would be used.

If a sensor 123 is implemented to measure temperature at the end of hose, the HBT power 43*b* would be adjusted according to the feedback control loop to maintain target EOH_T 44*a*. In this case, the neural network model (HBT) 121 would be bypassed. But, the patient contribution model (C) 50 would still be used to calculate EOH_T 44*a* from Mask Temperature targets 42*a*.

If a sensor 122 is implemented to measure humidity at the end of hose, the HP temperature/power 43*a* will be adjusted according to the feedback control loop to maintain target EOH humidity 44*b*. In this case, the neural network model (HP) 120 would be bypassed. But, the patient contribution model (AH) 50 would still be used to calculate EOH AH 44*b* from Mask AH targets 42*e*.

The humidity control model 120 as shown in can be a machine learning algorithm such as a neural network model or set of equations. A neural network model can be implemented in the controller to predict IP 43*a* and HBT settings 43*b* under different conditions, to achieve EOH targets (AH and T) 44*b*, 44*a*. The model 120 is trained using known inputs and outputs parameters from experimental data to mimic the relationships of the physical system. It is then implemented in the controller to predict the required settings output using a different set of inputs. Preferably, the HP model 120 runs first. This model determines the HP temperature 43*a* to maintain target EOH AH 44*b* under different conditions (ambient T, ambient AH and flow). The HBT model 121 takes HP setting 43*a* as input and controls HBT power 43*b* to compensate for the remaining EOH_T 44*a* requirement under different conditions (ambient T and flow).

The model can optionally comprise additional functionality to take into account another effect. As the water level in the chamber decreases over night due to water chamber geometry, the moisture pick-up capability and therefore the level of humidity being delivered decreases as well. By compensating for the water level decline, a constant level of humidity can be maintained throughout the night.

It would be done using the following steps:

Step 1—Calculate the Water Level Estimate

A water level estimate will be calculated using the inputs: ambient absolute humidity (Amb_AH), target end of hose output humidity (EOH_AH), average flow (L/min) and CPAP run time for the night, as follows.

The Initial WL (water level at the start of the therapy) can be assumed to be full chamber capacity.

Unit AH=EOH_AH−Amb_AH [AH added by CPAP in mg/L]

Evap. Rate=Unit AH*Average flow [evaporation rate in mg/min]

Water evaporated (mg)=Evap. Rate*Run time (hours)*60

Water level (mg or ml)=Initial WL−Water evaporated

Step 2—Calculating IP Setting

A mathematical model was described above with reference to FIG. 10 that relates the output humidity (or moisture pick up) as a function of heater-plate temperature, ambient temperature, input humidity and flow rate. The water level will be added as an input to the model as well. By rearranging this equation, we can get the heater-plate temperature setting. Alternatively, the water level can be added as an input to the neural network model.

1.2.6 Humidity and Temperature Control Models

An example of the mathematical HP 120 and HBT 121 models will now be described in more derail. The model is divided into 2 subsystems: humidity model (mainly humidifier chamber) 120 and temperature model 121 (mainly heated breathing tube). The models described below relate to a particular humidification breathing apparatus configuration. If the configuration changes, the equations will change. Referring back to FIG. 2, the breathing apparatus configuration has a chamber to hold about 400 ml of water, which is on top of a heater-plate, to evaporate the water in the chamber. There are sensors to measure the temperature of the heater-plate $C(T_{HPL})$ 119, which is fed into a PID feedback loop to maintain constant temperature by varying the supplied power. The incoming air flows over the water surface and picks up humidity. This humidity is carried through the hose 101, which is heated across its surface using the HBT (heater in the breathing tube) 101*a* in order to prevent rainout due to drop in temperature. The power in the tube ($P_{HBT}$) is controlled to get the desired temperature 44*a* at the end of the hose as previously described.

1.3 Alternative Embodiments

The above is one embodiment. Many others will be envisaged by those skilled in the art. Different implementations of (that is, different equations defining) the target temperature and humidity models 50 could be envisaged, along with different heater plate 120 and heated breathing tube 121 control models and implementations. Furthermore, the embodiment above uses the end of hose as the target point and the model used relates to the patient contribution that influences the humidity and temperature of the mask contributions. Other target points in the flow path of the breathing apparatus could be used, with the appropriate models used to compensate for contributions to humidity and temperature made by the downstream portions of the breathing apparatus. For example, the humidifier outlet could be used as the target point and the model would take into account patient and breathing tube contributions.

In one alternative embodiment, there is no heated breathing tube (that is a breathing tube without heating) and the only control parameter is the heater plate temperature 119. This means that AH 42*e* and temperature 42*d* in the mask cannot be independently controlled as both will be determined by the heater plate setting.

An equation can be used to determine the HP setting for the particular ambient temperature, ambient humidity, average flow and desired mask_RH or EOH_RH.

Embodiments described herein refer to the mask humidity and the mask temperature as the desired temperature/humidity proximate the patient, although this should not be considered limiting. Models could be created for achieving desired temperatures/humidities at other points in the flow path.

In further embodiments, it is possible to estimate parameters (patient exhaled humidity and temperature and tidal volume) based on more information about patient (height, weight, lung volume, age, gender, BMI etc) or surroundings (ambient temperature, inhaled temperature etc), or if the patient is nose breathing or mouth breathing.

Another way to represent the average humidity and temperature in the mask when patient breath may not be assumed as sinusoidal is:

$$\text{Mask Humidity}=\text{function}(V_{LUNG},\text{RF},J_B,h_C,h_P)$$

$$\text{Mask Temperature}=\text{function}(V_{LUNG},\text{RF},J_B,T_C,T_P,T_A)$$

Where RF=respiratory frequency.

An empirical relation for tidal volume via Body Surface Area (BSA), body Weight (W) and body Height (H) can be devised so these can be replaced instead of $V_{LUNG}$ in the above function.

Also, the RF in the above function can be replaced by br_period.

List of Parameters

Throughout this specification, various parameters are used. In some cases, the same parameter is represented by different symbols or acronyms in different equations. For clarity, a set of parameters and their symbols used in equations is set out below.

The desired absolute humidity at the mask is referred to as Mask_AH, $M_h$, $h_M$, Mask Humidity, $AH_{mixture}$, $AH_{mask}$.

The desired relative humidity at the mask is referred to as Mask_RH.

The desired temperature at the mask is referred to as Mask_T, $M_t$, $T_M$, Mask Temperature, $T_{mask}$.

The absolute humidity of the air at the patient end of breathing tube is referred to as EOH_AH, $h_C$, $AH_{CPAP}$.

The relative humidity of the air at the patient end of the breathing tube is referred to as EOH_RH.

The temperature of the air at the patient end of the breathing tube is referred to as EOH_T, $T_C$, $T_{CPAP}$.

The patient exhaled absolute humidity is referred to as Patient_AH, $h_P$, Patient humidity, $AH_{Patient}$.

The patient exhaled temperature is referred to as Patient_T, $T_P$, Patient temperature, $T_{Patient}$.

The generally constant flow rate leaving the bias holes of the mask (plus any leak through the mask) is referred to as Average Flow, Avg Flow, $J_B$, av, Flow.

The amplitude of the assumed sinusoidal patient flow rate is referred to as the Peak Flow, A.

The ambient temperature is referred to as Amb_T, $T_A$, Amb. Temperature, Ambient temperature, $T_{amb}$.

The ambient humidity is referred to as Amb_AH, Ambient humidity.

The specific heat and (average) density of the air at constant (average) process pressure are referred to as $C_P$ and ρ respectively.

The effective heat conduction coefficient through the mask is referred to as $k_{eff}$.

The surface area of the mask is referred to as S.

The heater plate is referred to as HP.

The heater in the breathing tube is referred to as HBT.

The temperature of the heater-plate is referred to as $T_{HPL}$.

The power in the heated tube is referred to as $P_{HBT}$.

The neural network is referred to as NN.

The tidal volume per breath is referred to as $V_{LUNG}$.

The time period of the breath is referred to as br_period.

The respiration frequency is referred to as RF.

Volumetric flow rate of the CPAP is referred to as $V_{CPAP}J_C$.

Volumetric flow rate of the patient breath is referred to as $V_{Patient}$, $J_P$.

Volumetric flow rate going out through the bias holes is referred to as $V_{bias}$, $J_B$, $V_{total}$.

Volume of the mask is referred to as $V_{mask}$.

Absolute humidity of the air in the mask is referred to as $AH_{mask}$.

The heat loss to ambient through the mask is referred to as $Q_{lost}$.

The forced convection resistance inside the mask is referred to as $R_{in}$.

The conduction resistance through the mask is referred to as $R_{cond}$.

The natural convection resistance from mask to ambient is referred to as $R_{out}$.

The temperature of the inner surface of the mask is referred to as $T_{inWall}$.

The temperature of the outer surface of the mask is referred to as $T_{outWall}$.

The invention claimed is:

1. A humidification breathing apparatus for generating and delivering humidified air to a patient at a desired humidity proximate the patient, the humidification breathing apparatus comprising:

an air flow path comprising an exhaust pathway open to ambient air, a heater, and a controller configured to control operation of the humidification breathing apparatus, wherein the controller is configured to:

receive the desired humidity to be supplied to the patient, determine an estimate of a patient contribution to humidity based on patient exhaled flow and an estimated patient exhaled humidity value, determine a target humidity at a target point by subtracting the estimate of the patient contribution from the desired humidity, the target point being located upstream of a patient delivery point in the air flow path, and operate the humidification breathing apparatus by controlling a power provided to the heater to heat the humidified air to achieve the target humidity when gases within the air flow path reach the target point wherein the estimated patient exhaled humidity value comprises at least one of:

a predetermined value, or a calculated value from one or more physiological patient characteristics, wherein the one or more physiological patient characteristics comprise one or more of BMI, height, weight, or body volume.

2. The humidification breathing apparatus according to claim 1, further comprising a conduit coupled to a patient interface, the conduit and the patient interface forming part of the air flow path.

3. The humidification breathing apparatus according to claim 2, wherein the target point in the air flow path where the controller is configured to control humidity is at or near an end of the conduit coupled to the patient interface.

4. The humidification breathing apparatus according to claim 2, wherein the patient interface is a mask and the controller controls humidity at the target point in the air flow path to achieve the target humidity calculated from the estimated patient exhaled humidity value and the patient exhaled flow using a model, a relationship between the target humidity and the estimated patient exhaled humidity value and the patient exhaled flow being based on a water vapour mass flow balance into and out of the mask.

5. The humidification breathing apparatus according to claim 4, wherein the water vapour mass flow balance is $$\underbrace{\left\langle \overset{\bullet H_2O}{m_M} \right\rangle}_{flow\ out} = \underbrace{\left\langle \overset{\bullet H_2O}{m_P} \right\rangle + \left\langle \overset{\bullet H_2O}{m_C} \right\rangle}_{flow\ in},\ [\text{mg H}_2\text{O sec}^{-1}]$$

wherein a water vapour mass flow out averaged over 1 breathing cycle $$\left\langle \overset{\bullet H_2O}{m_M} \right\rangle$$

equals an amount of water vapour present in air mixed in the mask and going out through exhaust/bias holes, wherein water vapour mass flow from the patient averaged over 1 breathing cycle $$\left\langle \overset{\bullet H_2O}{m_P} \right\rangle$$

is a function of humidification breathing apparatus delivered humidity, the estimated patient exhaled humidity value and a patient peak flow, wherein water vapour mass flow from the humidification breathing apparatus averaged over 1 breathing cycle $$\left\langle \overset{\bullet H_2O}{m_C} \right\rangle$$

is a function of humidification breathing apparatus delivered humidity and flow.

6. The humidification breathing apparatus according to claim 4, wherein the relationship is defined by:

$$\text{EOH\_AH}=f(A,J_B,M_h,h_p),$$

wherein hp is the estimated patient exhaled humidity value, wherein A is a patient peak flow, wherein $J_B$ is an average flow, wherein $M_h$ is the target humidity, wherein EOH_AH is an end of hose humidity.

7. The humidification breathing apparatus according to claim 4, wherein the relationship is defined by:

$$\text{EOH\_AH}=(\text{Mask\_AH}-(A/(J_B*pi))*\text{Patient\_AH})/(I-A/(J_B*pi)),$$

wherein A is a patient peak flow, wherein $J_B$ is an average flow, wherein Patient_AH is humidity of air exhaled by the patient, Mask_AH is a mask absolute humidity, and EOH_AH is an end of hose humidity.

8. The humidification breathing apparatus according to claim 2, wherein the target point in the air flow path where the controller is configured to control humidity is at or near an outlet of the humidification breathing apparatus.

9. The humidification breathing apparatus according to claim 1, further comprising a flow sensor to sense the patient exhaled flow.

10. The humidification breathing apparatus according to claim 1, wherein the patient exhaled flow comprises one or more characteristics of flow, being one or more of:

average flow rate, peak flow rate, or tidal volume.

11. The humidification breathing apparatus according to claim 1, wherein the controller is further configured to operate the humidification breathing apparatus to control humidity based on mask information.

12. The humidification breathing apparatus according to claim 1, wherein the exhaust pathway is downstream of the target point.

13. The humidification breathing apparatus according to claim 1, wherein the exhaust pathway comprises exhaust/bias holes.

14. A method of generating and delivering humidified air to a patient at a desired humidity proximate the patient comprising:

controlling operation of a humidification breathing apparatus using a controller, wherein the controller is configured to:

receive the desired humidity to be supplied to the patient, determine an estimate of a patient contribution to humidity based on patient exhaled flow and an estimated patient exhaled humidity value, determine a target humidity at a target point by subtracting the estimate of the patient contribution from the desired humidity, the target point being located upstream of a patient delivery point in an air flow path comprising an exhaust pathway open to ambient air, and operate the humidification breathing apparatus by controlling power provided to a heater to heat the humidified air to achieve the target humidity when gases within the air flow path reach the target point, wherein the estimated patient exhaled humidity value comprises at least one of:

a predetermined value, or a calculated value from one or more physiological patient characteristics, wherein the one or more physiological patient characteristics comprise one or more of BMI, height, weight, or body volume.

15. The method according to claim 14, wherein the target humidity is calculated from the estimated patient exhaled humidity value and the patient exhaled flow using a model, a relationship between the target humidity, the estimated patient exhaled humidity value and the patient exhaled flow being based on a balance of water vapour mass flow into and out of a mask coupled to the humidification breathing apparatus.

16. The method according to claim 14, wherein the exhaust pathway is downstream of the target point.

17. The method according to claim 14, wherein the exhaust pathway comprises exhaust/bias holes.

* * * * *